United States Patent [19]

Yabe et al.

[11] Patent Number: 4,918,521
[45] Date of Patent: Apr. 17, 1990

[54] SOLID STATE IMAGING APPARATUS

[75] Inventors: Hisao Yabe; Hisao Ogiu; Toshiyuki Takara; Koji Takamura; Masaaki Nakazawa; Akinobu Uchikubo, all of Hachiouji; Tomoaki Sato, Higashiyamatoshi; Atsushi Miyazaki; Akibumi Ishikawa, both of Hachiouji; Takeaki Nakamura, Hino, all of Japan

[73] Assignee: Olympus Optical Co., Ltd., Tokyo, Japan

[21] Appl. No.: 143,995

[22] Filed: Jan. 14, 1988

[30] Foreign Application Priority Data

Jan. 20, 1987 [JP] Japan .................................. 62-11013
Feb. 27, 1987 [JP] Japan .................................. 62-44481

[51] Int. Cl.[4] .......................... H04N 7/18; A61B 1/06
[52] U.S. Cl. .......................................... 358/98; 128/6; 358/229
[58] Field of Search ...................... 358/98, 93, 213.11, 358/229; 128/4, 6, 776

[56] References Cited

U.S. PATENT DOCUMENTS

| | | | |
|---|---|---|---|
| 4,491,865 | 1/1985 | Danna et al. ............................ | 358/98 |
| 4,573,450 | 3/1986 | Arakawa ................................ | 128/6 |
| 4,575,805 | 3/1986 | Moermann et al. ................. | 128/776 |
| 4,651,202 | 3/1987 | Arakawa ............................... | 358/98 |
| 4,677,471 | 6/1987 | Takamura et al. ................... | 358/98 |
| 4,682,219 | 7/1987 | Arakawa ............................... | 358/98 |
| 4,692,608 | 1/1987 | Cooper et al. ......................... | 128/6 |
| 4,745,470 | 5/1988 | Yabe et al. ............................. | 358/98 |
| 4,757,805 | 7/1988 | Yabe ....................................... | 358/98 |

FOREIGN PATENT DOCUMENTS 61-163315 7/1986 Japan .

Primary Examiner—John K. Peng
Attorney, Agent, or Firm—Armstrong, Nikaido, Marmelstein, Kubovcik & Murray

[57] ABSTRACT

This solid state imaging apparatus is provided within the tip part of an insertable part of an endoscope and is provided with an image forming optical system for forming images. This image forming optical system forms an optical image on the imaging surface of a solid state imaging chip provided in the rear of this image forming optical system. This solid state imaging chip is affixed to a circuit substrate extending substantially at right angles with the imaging surface and electrically connected with the solid state imaging chip. This circuit substrate is connected with a signal cable transmitting input and output signals of the solid state imaging chip.

12 Claims, 11 Drawing Sheets

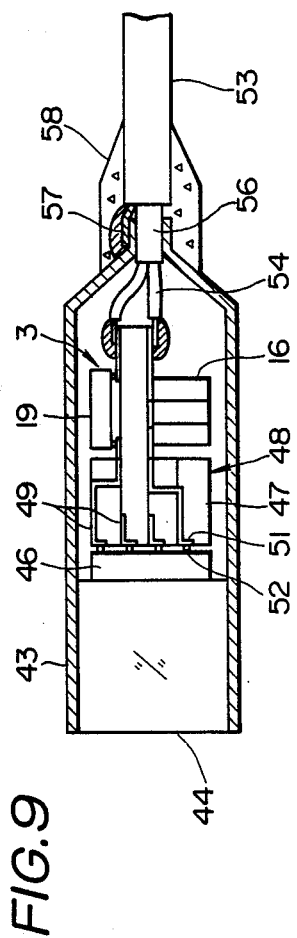
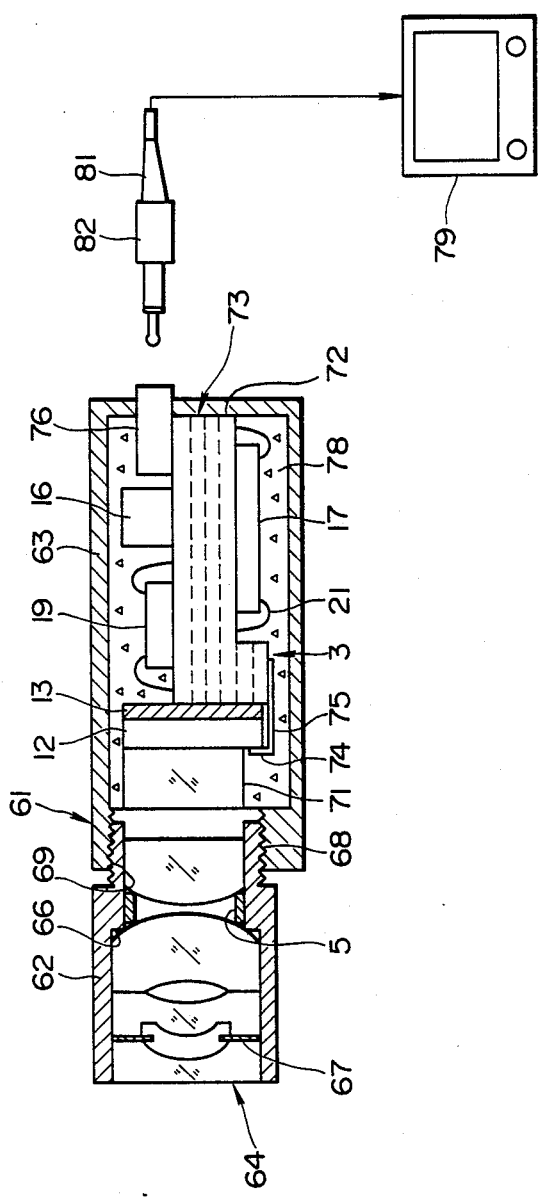
FIG.9
FIG.10

SOLID STATE IMAGING APPARATUS

FIELD OF THE INVENTION

This invention relates to solid state imaging apparatus capable of being made smaller.

BACKGROUND OF THE INVENTION

Various electronic endoscopes wherein such solid state imaging device as a charge coupled device (CCD) is used as an imaging means are recently suggested.

It is preferable that the insertable part of an electronic endoscope using the above mentioned solid state imaging device is made as small as possible in the diameter. However, for that purpose, it is necessary that the solid state imaging apparatus to be embedded into the tip of the insertable part of the endoscope should be made small.

In a conventional solid state imaging apparatus, as disclosed in the patent gazette of Japanese patent laid open No. 163315/1986, a solid state imaging chip is provided parallelly with the surface of a base member and is arranged at right angles with the optical axis of an objective lens, such electronic parts as an amplifying circuit and a driving circuit for producing various driving clocks are fitted to another substrate different from the base member, the substrate is then connected to the back surface of the base member and the above mentioned electronic parts are enclosed on the periphery with an electric shielding member or the like so as to be packaged.

In the above mentioned solid state imaging apparatus, there are defects that it is necessary to electrically connect the base member on which the solid state imaging chip is arranged and the substrate on which the electronic parts are fitted with each other, a space is required in the connecting part and therefore the outside diameter of the package is large and that, in case the package of this solid state imaging apparatus is provided within the endoscope tip part, the outside diameter of the endoscope tip part will be large and the length of the rigid part of the endoscope tip part will be large. Further, as the connecting parts increase as between the solid state imaging chip and the base member and between the base member and substrate, more defective products will be produced in the producing step and the reliability itself will reduce.

Also, as disclosed in the specification of U.S. Pat. No. 4,573,450, a solid state imaging chip is provided parallelly with the surface side of a base member and is arranged parallelly with the optical axis of an objective so that the optical axis may be bent by using such optical part as a prism and led to the solid state imaging chip.

The above mentioned solid state imaging apparatus has defects that, as not only the size of the prism but also the thickness of the cover glass provided on the surface of the solid state imaging chip, the thickness of the solid state imaging chip itself and the thickness of the base member are in the diametral direction of the endoscope, the tip part of the endoscope will have to be thick.

OBJECT AND SUMMARY OF THE INVENTION

An object of the present invention is to provide a solid state imaging apparatus wherein the connection of the solid state imaging chip with the base member is simple and positive, the occupied space is small, the electronic parts can be arranged by effectively using a small space, the reliability is improved and the size can be made small.

According to the present invention, a solid state imaging chip is arranged substantially at right angles with a circuit substrate so that the solid state imaging chip, circuit substrate and electronic parts may be arranged three-dimensionally.

The other features and advantages of the present invention will become apparent enough with the following explanation.

BRIEF DESCRIPTION OF THE DRAWINGS

FIG. 1 is a magnified sectioned view on line B—B' in FIG. 2 showing an industrial endoscope tip part internally fitted with a solid state imaging apparatus.

FIG. 2 is a magnified sectioned view on line A—A' in FIG. 1.

FIG. 3 is a schematic perspective view of an endoscope tip part.

FIG. 4 is an explanatory diagram showing the formation of an essential part.

FIG. 5 is a magnified sectioned view on line D—D' in FIG. 6 showing a bronchial endoscope tip part internally fitted with a solid state imaging apparatus.

FIG. 6 is a magnified sectioned view on line C—C' in FIG. 5.

FIG. 9 is a sectioned view of a TV camera having a built-in imaging apparatus of the fifth embodiment of the present invention.

FIG. 10 is a sectioned view of a TV camera having a built-in imaging apparatus of the sixth embodiment of the present invention.

FIG. 15 is a magnified sectioned view of an endoscope tip part.

FIG. 16 is a sectioned view in the direction of E—E' in FIG. 15.

FIG. 17 is a sectioned view in the direction of F—F' in FIG. 15.

DETAILED DESCRIPTION OF PREFERRED EMBODIMENTS

Figure 1:
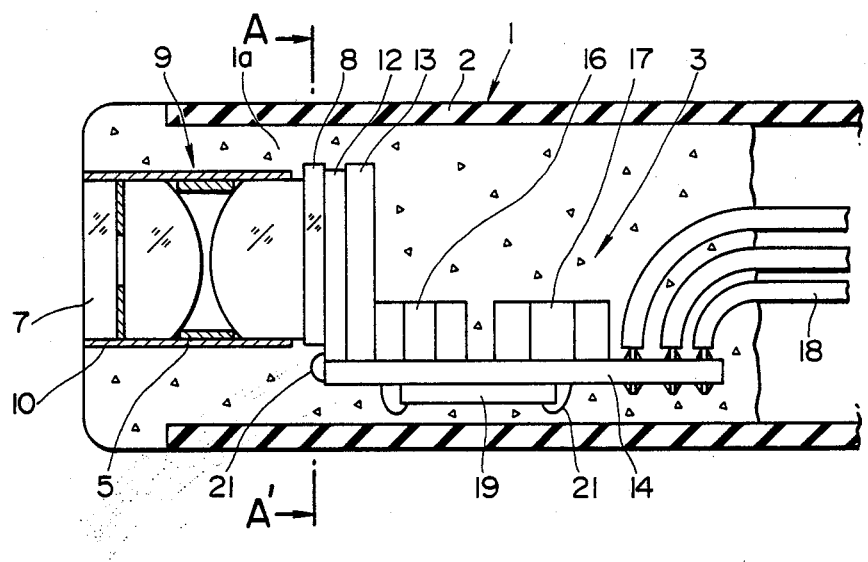
FIGS. 1 to 4 relate to the first embodiment of the present invention.
Figure 2:
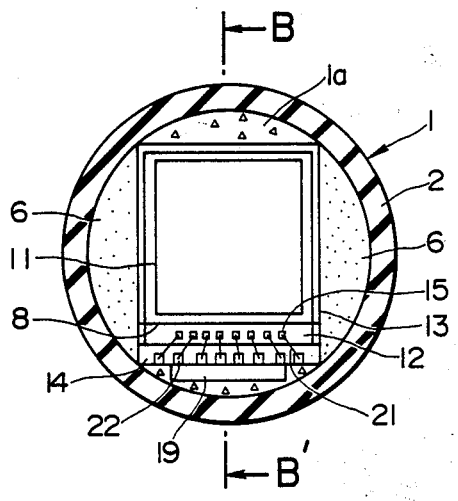
Figure 3:
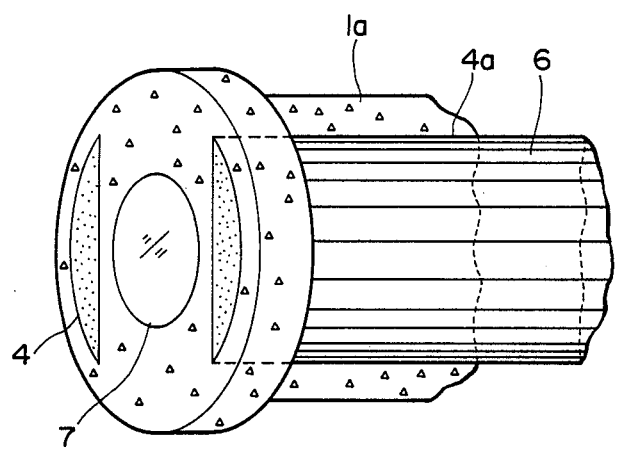
Figure 4:
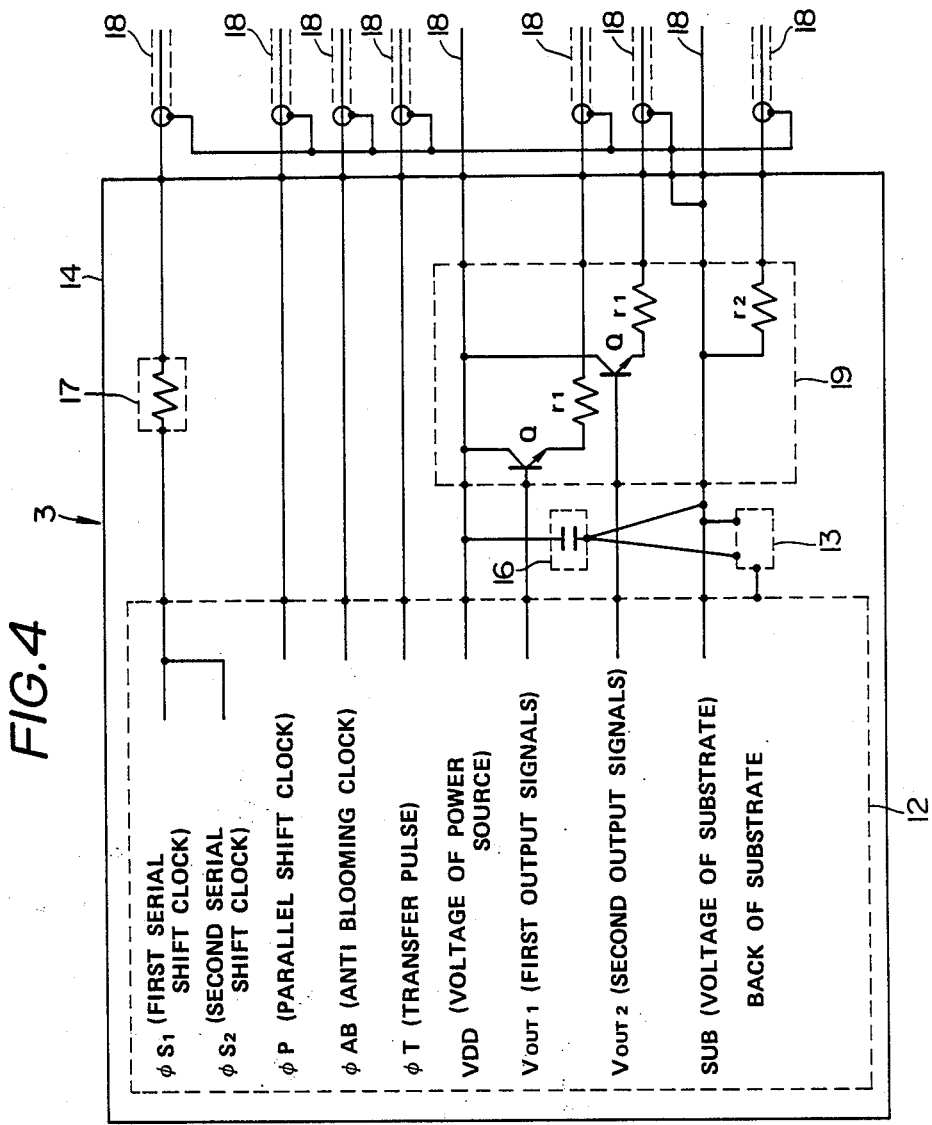

The present invention shall be concretely explained in the following with reference to the drawings:

FIGS. 1 to 4 relate to the first embodiment of the present invention. FIG. 1 is a magnified sectioned view on line B—B' in FIG. 2 showing an industrial endoscope tip part internally fitted with a solid state imaging apparatus. FIG. 2 is a magnified sectioned view on line A—A' in FIG. 1. FIG. 3 is a schematic perspective view of an endoscope tip part. FIG. 4 is an explanatory diagram showing the formation of an essential part.

In this embodiment, the present invention is applied to an industrial endoscope.

In an endoscope tip part 1, a tip body 1a is formed of a filler, has in the lengthwise direction light guide inserting holes 4 through which are inserted a pair of meniscus-like light guides 6 on both sides of the tip side formed to be flange-like s shown in FIG. 3 and forms on the rear side in the lengthwise direction a pair of light guide incisions 4a communicating with the light guide inserting holes 4. A coating sheath 2 made of an insulating material and extended from the rear of the insertable part is fitted and connected to a step formed in the rear of the flange-like tip side.

A solid state imaging apparatus 3 is embedded with the corners substantially in contact with the outer peripheral part of the tip body 1a within the tip body 1a as held by the above mentioned light guides 6 in FIG. 2.

An objective lens system 9 formed of a plurality of lenses 7 positioned by an objective frame 10 and spacer 5 is embedded with the optical axis center in the lengthwise direction of the endoscope in front of the above mentioned solid state imaging apparatus 3.

A cover glass 8 which is also a color filter array is provided adjacently in parallel in the rear of the above mentioned objective system 9. In the rear of the above mentioned cover glass 8, a solid state imaging chip 12 die-bonded to a die-bonding pad member 13 formed of a brass plate, for example, gold-plated on both surfaces is arranged adjacently to the above mentioned objective system 9 so as to be substantially at right angles with the lengthwise direction of the endoscope and to have the projected part of the objective system overlapped.

By the way, the material forming the die-bonding pad member 13 may be plastics or ceramics as painted or baked with a conductive paint or plated with a metal.

In FIGS. 1 and 2, the die-bonding pad member 13 is slightly larger than the solid state imaging chip 12. Therefore, even if the position of the solid state imaging chip 12 is somewhat displaced, the solid state imaging chip 12 will not protrude beyond the die-bonding pad member 13 and a reference potential will be given over the entire back surface of the solid state imaging chip. By the way, in FIG. 2, the right and left ends and upper end of the die-bonding pad member 13 coincide respectively with the right and left ends and upper end of the cover glass. That is to say, the dimension in the right and left direction of the die-bonding pad member 13 is equal to the dimension in the right and left direction of the cover glass 8.

In the above mentioned solid state imaging chip 12, as shown in FIG. 2, an image area 11 of a square, for example, of 2.5 mm.×2.5 mm. is formed in the central part except the periphery and chip side bonding pads 15, for example, eight, are provided on one somewhat wide side of the periphery of this image area 11. By the way, the image area 11 consists of about 30,000 pixels of which the part of $2.5\phi$ is used.

In FIG. 1, in the lower rear of the above mentioned die-bonding pad member 13, a circuit substrate 14 of a thickness, for example, of about 0.3 mm. is provided in the lengthwise direction of the endoscope so as to be in contact with the outer periphery of the tip body 1a, that is, the inner periphery of the coating sheath 2. By such arrangement, the diameter of the tip body 1a can be made smallest and the small space can be utilized most effectively.

Conductor patterns are provided on both surfaces of the above mentioned circuit substrate 14, for example, a laminated ceramic condenser 16, chip resistance 17 and cables 18 are fitted to one surface and an IC chip 19 is connected to the other surface through bonding wires 21.

The above mentioned laminated ceramic condenser 16 is positioned on the front part of the circuit substrate 14. One electrode (GND on the circuit) (in a circuit formation in which one electrode 16 is earthed) is electrically and mechanically connected with the above mentioned die-bonding pad member 13.

By the way, the laminated ceramic condenser 16 may not be connected with the die-bonding pad member 13 but may be connected substantially at right angles with the circuit substrate 14 by using the end surface of the die-bonding pad member 13.

In FIG. 2, on the front end surface of the above mentioned circuit substrate 14, base side bonding pads 22, for example, eight, are provided and are connected through bonding wires 21 with a chip side bonding pads 15 provided on the solid state imaging chip 12.

The circuit fitted on the circuit substrate 14 is to amplify in the current an output video signal, for example, from the solid state imaging chip 12.

By the way, in the case of forming the bonding pad 22 on the end surface of the circuit substrate 14, in order to increase the smoothness of the end surface, the end surface may be ground and then metalized. Further, in order to minutely form a bonding pad pattern, the end surface may be pattern-printed rather than being so-called side-brazed. Otherwise, a pattern may be formed by laser-trimming after the entire end surface is metalized.

In FIG. 4, the solid state imaging chip 12 provided on the circuit substrate 14 has a VDD for an electrode voltage as of an external electrode, $V_{out\,1}$ and $V_{out\,2}$ for the first and second signal outputs, SUB for earthing, $\phi S_1$ and $\phi S_2$ for applying the first and second serial shift clocks, $\phi P$ for applying a parallel shift clock, $\phi T$ for applying a transfer pulse from the first shift register to the second shift register and $\phi AB$ for applying an antiblooming clock which are electrically connected with signal cables 18 through wirings provided on the circuit substrate 14. The $\phi S_1$, $\phi S_2$, $\phi P$, $\phi AB$, $\phi T$, $V_{out\,1}$ and $V_{out\,2}$ of the above mentioned signal cables 18 are of high frequencies and therefore become noise sources. Therefore, shielding wires are used for their signal lines. The VDD and SUB do not become noise sources for the outside and therefore single lines are used for their transmission.

The above mentioned $V_{out\,1}$ and $V_{out\,2}$ are provided on the circuit substrate 14 and are input into current amplifiers formed in an IC chip 19. That is to say, the $V_{out\,1}$ and $V_{out\,2}$ are applied to the bases of a pair of transistors Q, are electrically amplified and are output from the emitters. The signals output from the respective emitters pass through matching printed resistances r1 and are input into a signal processing circuit not illustrated on the base side. Further, an equivalent resistance r2 provided on the IC chip 19 is connected with the SUB and a dummy is output in the shielding wire as a signal line.

The laminated ceramic condenser 16 is connected with the VDD, SUB and die-bonding pad member 13. The die-bonding pad member 13 is connected with the back surface of the solid state imaging chip 12 and SUB.

Further, a serial shift clock is to be applied to the $\phi$S1 and $\phi$S2 through a chip resistance 17 for damping.

Now, the solid state imaging chip 12 to which a driving clock has been applied through the signal cable 18 outputs an observed image formed on the imaging surface as a picture image signal by the photoelectric conversion. This picture image signal is amplified by the IC chip 19 forming an amplifying circuit and is delivered to a signal processing circuit not illustrated. In this signal processing circuit, a composite video signal produced from the picture image signal is output to a monitor not illustrated to display the observed image on the picture surface of the monitor.

In this embodiment, as the base side bonding pads 22 and chip side bonding pads 15 of the circuit substrate 14 fitted with the electronic parts are connected with each other through bonding wires 21 and further the circuit substrate 14 is arranged substantially at right angles with the solid state imaging chip 12, a three-dimensional high density fitting is made possible and the solid state imaging apparatus 3 can be made small. Therefore, in case this embodiment is used for an endoscope, the insertable part tip can be made small in the diameter and can be made short.

Figure 5:
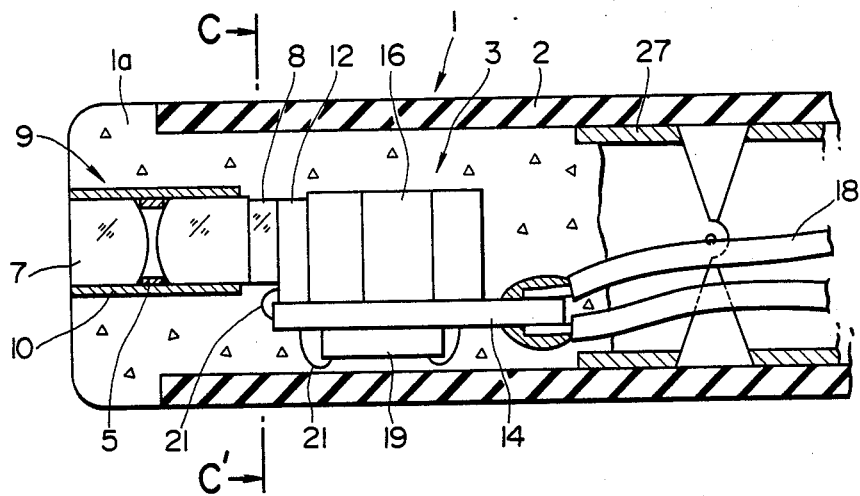
FIGS. 5 and 6 relate to the second embodiment of the present invention.
Figure 6:
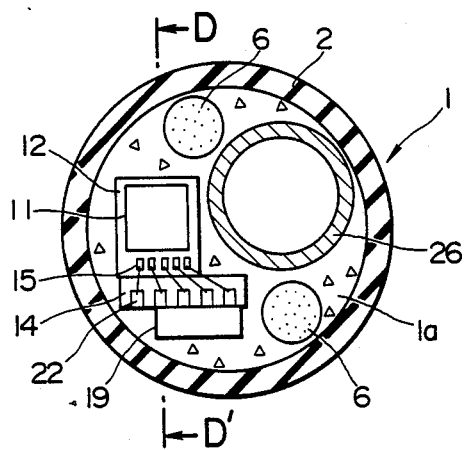

FIGS. 5 and 6 relate to the second embodiment of the present invention. FIG. 5 is a magnified sectioned view on line D—D' in FIG. 6 showing a bronchial endoscope tip part internally fitted with a solid state imaging apparatus. FIG. 6 is a magnified sectioned view on line C—C' in FIG. 5.

This embodiment is to apply the present invention to a bronchial endoscope.

In FIG. 6, a tip body 1a is formed of a filler in an endoscope tip part 1. As shown in FIG. 6, in this tip body 1a formed to be in the form of a flange in the front part, a pair of light guides 6 and a channel 26 for a forceps are inserted parallelly in the lengthwise direction and further a solid state imaging apparatus 3 is embedded in the lengthwise direction.

In the rear part of the above mentioned tip body 1a, curvable frames 27 connected rotatably with each other and made curvable vertically and horizontally are secured in the tip positions and the outer periphery is coated with a coating sheath 2 to be of an outer diameter, for example, of 5.6 mm.

The tip body 1 is plated or painted with a conductor paint to form a conductive layer on the contact surface with the above mentioned coating sheath which reaches a video processor (camera controlling unit) not illustrated through the curvable frames 27 to develop a shielding effect.

In the front part of the interior of the above mentioned tip body 1a, as shown in FIG. 5, an objective system 9 formed of a plurality of lenses 7 positioned by an objective frame 10 and spacer 5 is embedded with the optical axis center in the lengthwise direction of the endoscope.

A cover glass 8 is provided parallelly adjacently to the rear of the above mentioned objective system 9. Further, in the rear of the cover glass 8, a solid state imaging chip 12 of dimensions, for example, of 1.65 mm.×1.4 mm. is arranged adjacently to the above mentioned objective system 9 so as to be substantially at right angles with the lengthwise direction of the endoscope and to have the projection of the objective system 9 overlapped on it.

The above mentioned solid state imaging chip 12 has an image area 11 of a square of 1 mm.×1 mm. and about 10,000 pixels formed in the central part except the periphery. Chip side bonding pads 15, for example, five, are provided on one somewhat wider side on the periphery of this image area 11.

A circuit substrate 14 of a multilayer, for example, two-layer substrate of a total thickness of 0.5 mm. provided parallelly with the lengthwise direction of the endoscope is to be in contact on the front upper surface with the lower end surface of the above mentioned solid state imaging chip 12. Further, the center of the solid state imaging chip 12 is provided as displaced in the horizontal direction in FIG. 6.

For example, a laminated ceramic condenser 16 and signal cable 18 are fitted to one surface of the above mentioned circuit substrate 14 and the signal cable 18 and an IC chip 19 are fitted to the other surface of the circuit substrate 14. By the way, the center of the IC chip 19 is provided as displaced in the horizontal direction in FIG. 6 with respect to the circuit substrate 14.

The above mentioned solid state imaging chip 12 is die-bonding directly with one electrode (GND on the circuit) (in the circuit formation in which one electrode of the laminated ceramic condenser 16 is earthed) of the laminated ceramic condenser 16.

In FIG. 6, on the front end surface of the above mentioned circuit substrate 14, base side bonding pads 22, for example, five, are provided and are connected with the chip side bonding pads 15 provided on the solid state imaging chip 12 through bonding wires 21. The spacing of the base side bonding pads 22 is larger than the spacing of the chip side bonding pads 15, because it is more difficult to provide the base side bonding pads on the end surface of the circuit substrate 14 than to provide the chip side bonding pads 15 on the solid state imaging chip 12.

By the way, an amplifying circuit is formed of this laminated ceramic condenser 16 and IC chip 19.

In FIG. 6, for example, the width in the diametral direction of the circuit substrate is provided to be larger than the width of the solid state imaging chip 12 and, as mentioned above, the solid state imaging chip 12 and IC chip 19 are provided eccentrically from the circuit substrate 14. Further, a forceps channel 26 is provided so as to be adjacent to the solid state imaging chip 12, to be in the displaced direction of the circuit substrate 14 with respect to the solid state imaging chip 12 and to be adjacent to the circuit substrate 14.

By the way, the thickness of each of the solid state imaging chip 12, cover glass 8 and IC chip 19 is 0.5 mm. and the inside diameter of the coating sheath 2 is 4.6 mm.

In this embodiment, the solid state imaging chip 12 to be used is smaller than in the first embodiment, the solid state imaging apparatus 3 is made smaller by directly die-bonding the laminated ceramic condenser and the space through which the forceps channel 26 and light guide 6 can be inserted is secured within the endoscope tip part 1 by providing the solid state imaging chip 12 and IC chip 19 eccentrically with respect to the circuit substrate 14.

The other formations, operations and effects are the same as in the first embodiment.

Figure 7:
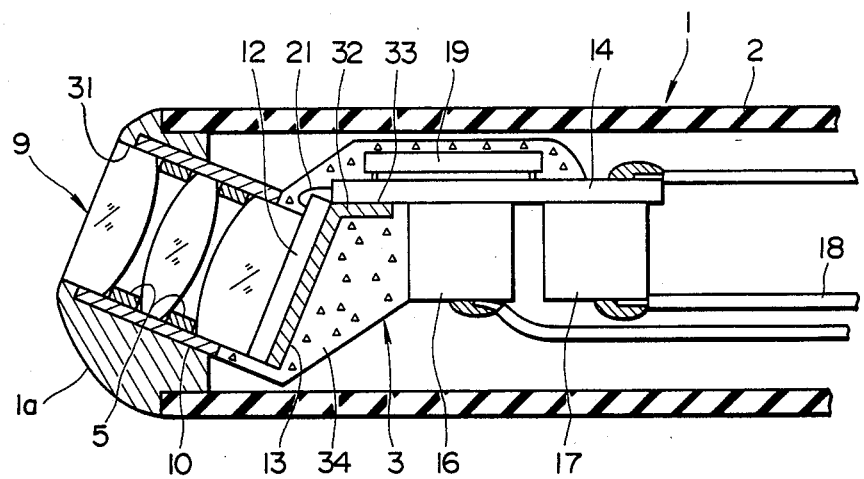
FIG. 7 is a sectioned view of an endoscope tip part having a built-in solid state imaging apparatus of the third embodiment of the present invention.

FIG. 7 is a sectioned view of an endoscope tip part having a built-in solid state imaging apparatus of the third embodiment of the present invention.

In this embodiment, the present invention is applied to a front oblique view type endoscope.

An endoscope tip part 1 is provided with a rigid substantially columnar tip body 1a. An observing through hole 31 obliquely upward inclined in the lengthwise direction of the endoscope tip part 1 is provided in the central part of this tip body 1.

An objective frame 10 in which the objective system 9 is positioned by spacers 5 is fitted and fixed within the observing through hole 31 so as to be exposed in the rear end part out of the tip body 1.

A solid state imaging chip 12 is overlapped on the rear end surface of the above mentioned objective system 9. Further, a die-bonding pad member 13 having a flange part 32 in the edge part on the oblique view direction side is overlapped on the rear end surface of this solid state imaging chip 12. The above mentioned flange part 32 has an angle somewhat larger than a right angle with the jointing plane of the above mentioned solid state imaging chip 12 with the die-bonding pad member 13. Further, the plane circuit substrate 14 provided with wirings is jointed with the flange surface 33 forming the flange part 32 so as to be parallel with the lengthwise direction of the endoscope tip part 1.

A flexible tubular coating sheath 2 is externally fitted and fixed to the rear end part of the above mentioned tip body 1a. In the space between this coating sheath 2 and circuit substrate 14, an IC chip 19 is electrically connected to the circuit substrate 14 by face-bonding which can make the height of the connecting part lower than by wire-bonding. Further, the solid state imaging chip 12 and circuit substrate 14 are electrically connected with each other through bonding wires 21.

On the surface opposed to the surface of the circuit substrate 14 on which the above mentioned IC chip 19 is provided, a laminated ceramic condenser 16 and chip resistance 17 are provided and electrically connected. This circuit substrate 14, laminated ceramic condenser 16 and chip resistance 17 are respectively separately directly soldered with signal cables 18 so as to be able to transmit signals to and from a signal processing circuit not illustrated provided on the base side.

Also, the solid state imaging chip 12, bonding wire 21, IC chip 19 and a part of the laminated ceramic condenser 16 are sealed with a sealing resin 34.

According to this embodiment, as the objective frame 10 is made oblique in viewing, a space is thereby formed within the endoscope tip part 1, the circuit substrate 14 is provided in this space, further the IC chip 19 is connected on the circuit substrate 14 by face-bonding, no flat land for connecting the signal cables 18 is provided on the circuit substrate and the signal cables 18 are soldered directly to the electronic parts, in case the circuit substrate 14 is made short and is provided within the endoscope tip part 1, the outside diameter of the endoscope tip part 1 can be made small and the rigid part can be made short.

The other formations, operations and effects are the same as in the first embodiment.

Figure 8:
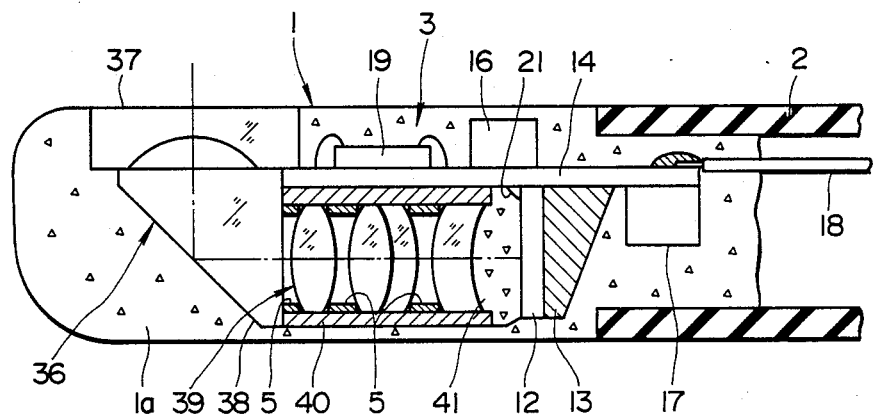
FIG. 8 is a sectioned view of an endoscope tip part having a built-in solid state imaging apparatus of the fourth embodiment of the present invention.

FIG. 8 is a sectioned view of an endoscope tip part having a built-in solid state imaging apparatus of the fourth embodiment of the present invention.

In this embodiment, the present invention is applied to a side view type endoscope.

An endoscope tip part 1 is provided with a tip body 1a formed to be columnar of such material high in the strength and moistureproofness as an epoxy, polyphenylene sulfide (PPS) or polyimide type resin. A solid state imaging apparatus 3 formed of an image forming optical system 36, solid state imaging chip 12, circuit substrate 14 and electronic parts is sealed within the above mentioned tip body 1a.

On the outer peripheral surface of the tip part of the above mentioned tip body 1a, an objective 37 forming the image forming optical system 36 is provided with the optical axis at right angles with the lengthwise direction of the endoscope tip part 1. On the back surface of this objective 37, a right angular prism 38 is provided so as to make the optical axis of the above mentioned objective 37 parallel with the lengthwise direction of the endoscope tip part 1 and to rearward bend it.

On the rear end surface of the above mentioned right angular prism 38, a circuit substrate 14 is provided so as to be parallel with the lengthwise direction of the endoscope tip part 1 and to be in contact on the front end surface with the rear end surface of the right angular prism 38. Further, an image forming lens frame 40 in which an image forming lens system 39 is positioned by spacers 5 is provided in contact on the front end surface with the rear end surface of the right angular prism 38.

The imaging surface of the solid state imaging chip 12 is positioned in the image forming position of the above mentioned image forming lens system and near the central part of the circuit substrate 14. This imaging surface side and the circuit substrate 14 are electrically connected with each other through a bonding wire 21 between the solid state imaging chip 12 and the image forming lens system 39. Further, a light transmitting resin 41 is sealed between the solid state imaging chip 12 and the image forming lens system 39.

On the back surface of the imaging surface of the above mentioned solid state imaging chip 12, a die-bonding pad member 13 formed, for example, of a brass plate gold-plated on both surfaces is provided in the form of a trapezoid as positioned near the middle part of the circuit substrate 14 so as to support the solid state imaging chip 12 from the circuit substrate 14.

On the other surface opposed to the surface on which the solid state imaging chip 12 is provided of the circuit substrate, a laminated ceramic condenser 16 and an IC chip are provided and, in the rear end part, a signal cable 18 transmitting signals is soldered.

On the rear part of the surface on which the solid state imaging chip 12 is provided, a chip resistance 17 is provided.

A flexible tubular coating tube 2 is externally fitted and fixed to the rear part of the above mentioned tip body 1a.

According to this embodiment, as the image forming lens system 40 is arranged on the back surface of the circuit substrate 14 on which the electronic parts are provided, the solid state imaging apparatus 3 can be made short and further, as the tip body 1a is formed of only a resin, the outside diameter of the tip part can be made small.

By the way, in this embodiment, the right angular prism 38 is provided for the solid state imaging apparatus 3 so as to enable side viewing but any other prism than the right angular prism may be used so as to enable oblique viewing.

The other formations, operations and effects are the same as in the first embodiment.

FIG. 9 is a sectioned view of a TV camera having a built-in imaging apparatus of the fifth embodiment of the present invention.

A solid state imaging apparatus 3 is provided with a rigid cylindrically formed housing 43. An objective 44 formed, for example, of a self-convergent type lens is internally fitted and fixed in the front end part within this housing 43. A rectangular and, for example, back surface illuminating type solid state imaging chip 46 is provided with the imaging surface in contact with the rear end surface of the objective 44. A multilayer substrate 48 formed by laminating, for example, four layers of substrates 47 is provided in the rear of this solid state imaging chip 46 so as to be contained within the projected area in the optical axial direction of the solid state imaging chip 46. The substrate 47, for example, in the third layer from below of this multilayer substrate 48 is extended rearward.

Conductor patterns 49 are provided on the above mentioned respective substrates 47. Flat lands 51 provided on the front end surfaces of the respective substrates 47 and the conductor patterns 49 provided on both surfaces of the above mentioned extended substrate 47 are electrically connected with each other. This flat land 51 is to be face-bonded with a bump 52 provided on the back surface of the imaging surface of the solid state imaging chip 46.

An IC chip 19 as an electronic part on one surface of the above mentioned extended substrate 47 and a laminated ceramic condenser 16 on the other surface are respectively face-bonded on the conductor patterns 49. Internal wires 54 of a bundled shielding wire 53 as signal cables are soldered to the rear part of the substrate 47 provided with these electronic parts.

The above mentioned housing 43 is squeezed in the rear part to be small in the diameter and to insert and secure a bundle 56 bundling the above mentioned internal wires 54. An integral shielding wire 57 of the bundled shielding wire 53 is soldered to the housing 43 to shield the housing 43. This connecting part is reinforced by a reinforcing resin 58 which has a sealing property to keep the interior of the housing 43 air-tight. By the way, the housing 43 is filled with an inert gas.

The above mentioned bundled shielding wire 53 is connected to a controlling apparatus having a signal processing circuit not illustrated. Further, the controlling apparatus is to be connected to a monitor not illustrated.

In this embodiment, as the multilayer substrate 48 fitted with the electronic parts is provided so as to be substantially at right angles with the solid state imaging chip 46 and to be contained within the projected area of the solid state imaging chip 46 and further the multilayer substrate 48 and solid state imaging chip 46 are face-bonded with each other to make the connecting space small, a three-dimensional high density fitting is made possible, the solid state imaging apparatus 3 can be made small and, therefore, in case the embodiment is used for an endoscope, the endoscope insertable part tip can be made small in the diameter and short.

The other formations, operations and effects are the same as in the first embodiment.

FIG. 10 is a sectioned view of a TV camera having a build-in imaging apparatus of the sixth embodiment of the present invention.

A TV camera 61 is formed of a columnarly formed rigid objective frame 62 and a TV camera body 63 formed of a rigid material and having a built-in solid state imaging apparatus 3.

In the above mentioned objective frame 62, an objective system 64 formed of plastic lenses or the like is so positioned as to hold a brightness diaphragm plate 67 with a spacer 5 and step 66. The objective frame 62 is made small in the diameter in the rear part and a male screw part 68 is provided in the position of this small diameter.

Within the above mentioned TV camera body 63, a female screw part 69 with which the above mentioned male screw part 68 can be screwed is provided in the front part and a moire removing filter 71 is provided in the rear of the female screw part 69 so that the center line may coincide with the optical axis of the above mentioned objective system 64. A solid state imaging chip 12 having a die-bonding pad member 13 secured to the opposite imaging surface side is provided with the imaging surface in contact with the rear end surface of this moire removing filter 71.

A multilayer ceramic substrate 73 formed by laminating a plurality of ceramic substrates 72 provided parallelly with the lengthwise direction center of the TV camera body 63 is provided with the front end surface in contact with the rear end surface of the above mentioned die-bonding pad member 13. This multilayer ceramic substrate 73 is formed, for example, of six layers of ceramic substrates 72 and the third or sixth layer from below is extended rearward. The first layer of the above mentioned multilayer ceramic substrate 73 is extended forward and, on its lower surface, a plurality of leads 75 provided with flange parts 74 in the front parts are provided so as to be connected to the internal wirings of the multilayer ceramic substrate 73.

The above mentioned flange part 74 is electrically connected with a bonding pad part not illustrated of the solid state imaging chip 12 by face-bonding.

A chip resistance 17 is provided on the lower surface of the ceramic substrate 72 of the third layer of the above mentioned multilayer ceramic substrate 73 and is connected to the internal wirings through bonding wires 21. Further, on the upper surface of the ceramic substrate 72 of the sixth layer, an IC chip 19 is wire-bonded and a laminated ceramic condenser 16 and a connector receiver 76 are respectively face-bonded.

The above mentioned connected receiver 76 is exposed through the rear end surface of the above mentioned TV camera body 63 so that a connector 82 provided at the end of a signal cable 81 extended from a monitor 79 may be removably connected to the connector receiver 76.

The interior of the above mentioned TV camera body 63 is sealed with such sealing material 78 high in the elasticity as a silicone type or urethane type bonding agent.

Now, the electronic parts provided on the multilayer ceramic substrate 73 are to drive the solid state imaging chip 12 and photoelectrically convert an observed image formed on the imaging surface of the solid state imaging chip 12 to produce a picture image signal. The picture image signal delivered to the monitor 79 through the connector 82 and signal cable 81 is processed to be converted to such reference video signal, for example, as an NTSC composite signal so that the observed image may be displayed on the picture surface of the monitor 79.

As in this embodiment, when the multilayer ceramic substrate 73 having internal wirings is arranged on the back surface of the solid state imaging chip 12, the TV camera body 63 can be made smallest in the contour.

Figure 11:
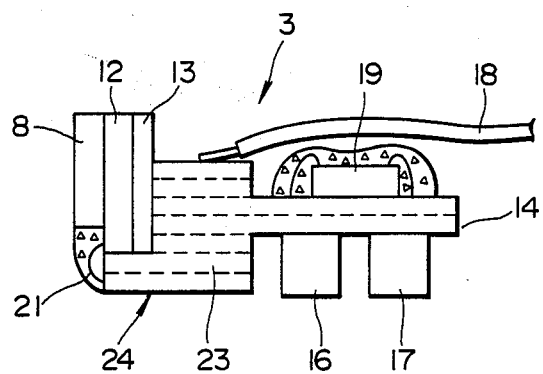
FIG. 11 is an explanatory view of a solid state imaging apparatus of the seventh embodiment of the present invention.

FIG. 11 is an explanatory view of a solid state imaging apparatus of the seventh embodiment of the present invention.

In this embodiment, a circuit substrate 14 is a multilayer ceramic substrate 24 formed by laminating, for example, seven layers of ceramic substrates 23 of a thickness of 0.2 mm. each.

Of the above mentioned multilayer substrate 24, for example, the fourth and fifth layers from below are extended rearward. A laminated ceramic condenser 16 and IC chip resistance 17 are fitted to one surface of these extended ceramic substrates 23 and an IC chip 19 is wire-bonded on the opposite surface. Also, the first and second layers from below of the multilayer ceramic substrate 24 are extended forward on the front end surface. A die-bonding pad member 13 formed, for example, of brass plate gold-plated on both surfaces is secured so as to be in contact with the upper surface of the ceramic substrate 23 of the second layer and the front end surfaces of the third to seventh layers. Further, the opposite imaging surface of the solid state imaging chip 12 is bonded to the front end surface of the die-bonding pad member 13. That is to say, the die-bonding pad member 13 is in contact with the second layer of the multilayer ceramic substrate 24.

Conductor patterns are provided on the contact surface of the above mentioned multilayer ceramic substrate 24 with the solid state imaging chip 12 and on the contact surface of the multilayer ceramic substrate 24 with the die-bonding pad member 13 and are conducted with the die-bonding pad member 13. That is to say, the die-bonding pad member 13 plays a role of an interlayer pattern (through hole) for the circuit substrate 14.

By the way, the multilayer ceramic substrate 24 is likely to lack and become irregular on the sides and corners. Therefore, when the solid state imaging chip 12 is to be directly die-bonded, the entire back surface of the solid state imaging chip 12 will not uniformly contact. Therefore, the die-bonding pad member 13 is provided to improve the adhesion.

By the way, the die-bonding pad member 13, solid state imaging chip 12 and cover glass 8 partly protrude out of the multilayer ceramic substrate 24 as clear from FIG. 11.

A square image area is formed in the central part except the peripheral side on the above mentioned solid state imaging chip 12. A chip side bonding pad not illustrated is provided on a somewhat widened side on the peripheral side of this image area 11. On the other hand, a base side bonding pad not illustrated is provided on the front end surface of the first layer of the multilayer ceramic substrate 24 and is connected with the above mentioned chip side bonding pad not illustrated through a bonding wire 21. The multilayer ceramic substrate 24 is not on the entire back surface of the die-bonding pad member 13 and is provided with a flat land for a cable 18 on the upper surface of the seventh layer.

By the way, as the multilayer ceramic substrate 24 is likely to lack on this side and the other side of the paper surface of the multilayer ceramic substrate 24, if the solid state imaging chip 12 is die-bonded directly to the multilayer ceramic substrate 24 without providing the die-bonding pad member 13, the solid state imaging chip 12 will protrude out of the multilayer ceramic substrate 24 by the lacked part of the multilayer ceramic substrate 24 to be a problem. In order to prevent it, it is necessary to make the dimension in the direction vertical to the paper surface of the multilayer ceramic substrate 24 larger than the dimension of the solid state imaging chip 12 by the dimension anticipated to be lacked on one side and the solid state imaging apparatus 3 and the endoscope tip part 1 containing it becomes thicker. On the other hand, the die-bonding pad member 13 of this embodiment is made of a metal and can be manufactured without producing a lack and therefore such problem is not produced.

Therefore, the dimension in the direction vertical to the paper surface of the die-bonding pad member 13 may be made substantially equal to the dimension of the solid state imaging chip 12 the same as in the vertical direction in FIG. 11 and therefore the solid state imaging apparatus 3 can be made small. By the way, the die-bonding pad member 13 in the direction vertical to the paper surface may protrude out of the multilayer ceramic substrate 24 the same as in the vertical direction in FIG. 11.

In this embodiment, as the electronic part is fitted to the multilayer ceramic substrate 23, a higher density three-dimensional fitting than in the first and second embodiments can be made.

Figure 12:
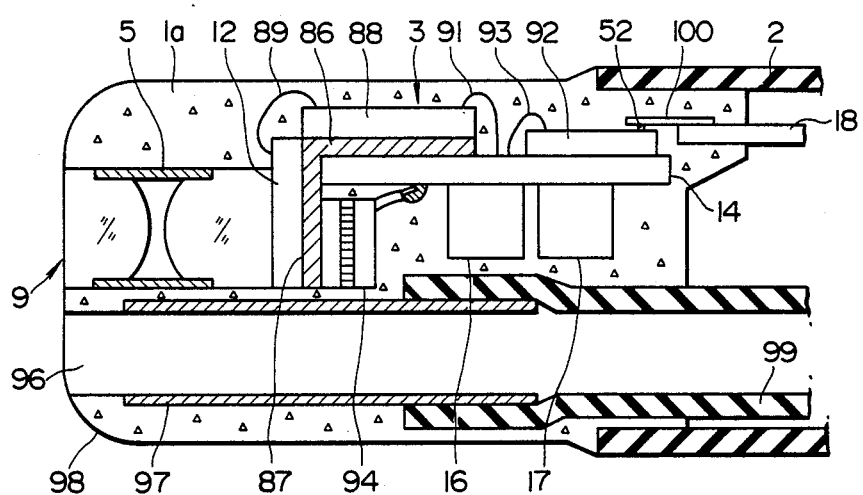
FIG. 12 is a sectioned view of a straight view type endoscope having a built-in imaging apparatus of the eighth embodiment of the present invention.

FIG. 12 is a sectioned view of the tip part of a straight view type endoscope containing the imaging apparatus of the eighth embodiment of the present invention. An objective system 9 formed of lenses fitted at both ends of a spacer 5 is provided on the tip surface of a tip body 1a provided in the endoscope tip part 1. A solid state imaging chip 12 is provided with its imaging surface contacted with the rear end surface of this objective system 9. A die-bonding pad member 87 having one edge part forming a flange part 86 bent substantially at right angles is die-bonded on the rear end surface of this solid state imaging chip 12. On one surface holding a right angle of the flange surfaces forming this flange part 86, a circuit substrate 14 is secured so as to be extended rearward on one surface from the flange part 86. An IC chip 88 is die-bonded to the other surface of the flange part and is connected with the solid state imaging chip 12 by a bonding wire 89 and with the circuit substrate 14 by a bonding wire 91.

An IC chip 92 is die-bonded to the surface secured to the flange part 86 in the rear of the above mentioned circuit substrate 14 and is connected with the circuit substrate 14 by a bonding wire 93. Further, a laminated ceramic condenser 16 and chip resistance 17 are fitted to the surface not secured to the flange part 86.

A bump 52 is provided on the rear part of the above mentioned IC chip 92. A plurality of leads 100 automatically bonded by tapes to the tip part of a flexible substrate 18 as signal cables are face-bonded to this bump 52.

Such cooling element 94 as, for example, a Peltier element is provided on the back surface of the bonding pad member 87 to which the above mentioned solid state imaging chip 12 is die-bonded to cool the solid state imaging chip 12 and IC chip 88. By thus cooling, the dark current of the solid state imaging chip 12 reduces, the S/N ratio improves and a damage by the heating of the IC chip 88 can be prevented.

The solid state imaging apparatus 3 formed of the objective, solid state imaging chip 12, die-bonding pad member 87 and electronic parts is sealed on the periphery together with a forceps channel tube 97 forming a forceps channel 96 with an epoxy, polyphenylene sulfide (PPS) or polyimide type resin or the like high in the strength and moistureproofness so as to form a tip body 1a which is columnar, is provided with a rounded part 98 on the tip edge and is formed to be somewhat larger in the diameter in the rear part. In the part formed to be larger in the diameter, a smaller diameter part is provided by a step and a flexible tubular coating tube 2 is externally fitted to this smaller diameter part.

A flexible forceps channel tube 99 is externally fitted to the rear part of the above mentioned forceps channel tube 97 and is sealed in the front end part within the tip body 1a. By the way, the above mentioned rounded part 98 is made to somewhat reach the above mentioned forceps channel 96 on the tip surface of the tip body 1a.

Now, the input and output signals of the solid state imaging chip 12 are connected to the IC chip 88 through the bonding wire 89. Of these input and output signals, one part is processed by the IC chip 88 but the other part passes through the IC chip 88 and is connected with the circuit substrate 14 through the bonding wire 91.

According to this embodiment, as the circuit substrate 14, cooling element 94, laminated ceramic condenser 16 and chip resistance 17 are arranged within the projected area from the imaging surface of the solid state imaging chip 12, the space within the tip body 1a can be three-dimensionally and effectively utilized and the outside diameter of the endoscope tip part 1 can be made smaller.

The other formations, operations and effects are the same as in the first embodiment.

Figure 13:
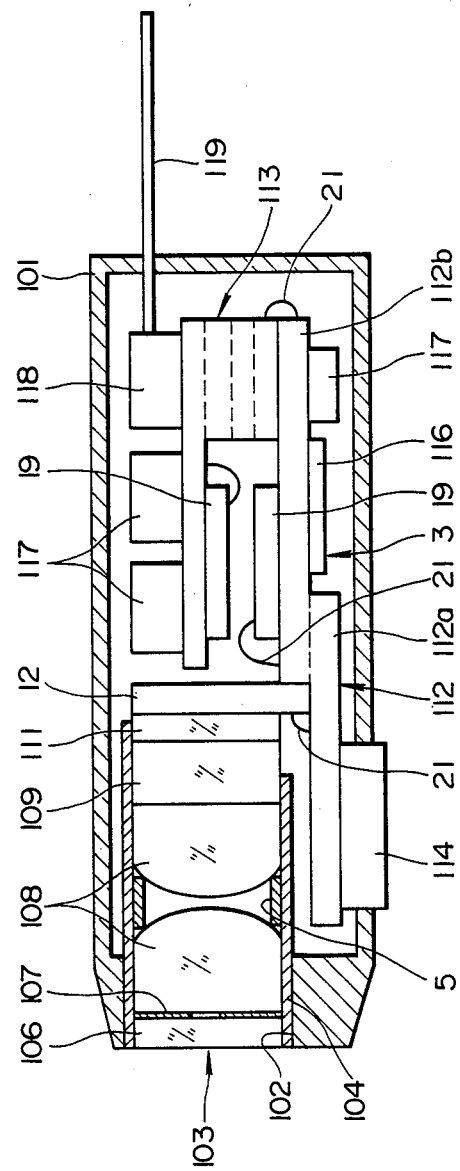
FIG. 13 is a sectioned view of a TV camera having a built-in imaging apparatus of the ninth embodiment of the present invention.

FIG. 13 is a sectioned view of a TV camera having a built-in imaging apparatus of the ninth embodiment of the present invention.

In this embodiment, the imaging apparatus of the present invention is applied to a TV camera.

An observing through hole 102 is provided on the front end surface of a TV camera body 101 formed of a rigid material. An objective frame 104 in which an objective system 103 is positioned by a spacer 5 is fitted and fixed in this observing through hole 102. This objective system 103 is formed of an infrared ray cutting filter 106, brightness stopping plate 107, image forming lens 108, moire removing filter 109 and color filter array 111 in the mentioned order from the front end surface side.

A solid state imaging chip 12 is provided in contact on the imaging surface with the rear end surface of the above mentioned color filter array 111, is provided at right angles with the upper surface near the central part of a substrate 112a forming a first circuit substrate 112 provided in parallel with the center line in the lengthwise direction of the TV camera body 101 and is electrically connected with the substrate 112a by a bonding wire 21. Further, on the lower surface of the substrate 112a, a switch 114 which can switch on and off a current source from a battery not illustrated provided within the TV camera body 101 is provided so as to expose the operating part through the TV camera body 101.

In the rear of the solid state imaging chip 12 on the upper surface of the above mentioned substrate 12a, a substrate 112b is provided as overlapped so as to be in contact on the front end surface with the back surface of the solid state imaging chip 12. An IC chip 19 and second circuit substrate 113 connected with the substrate 112b by bonding wires 21 are provided from the front on the upper surface of this substrate 112b and further, a printing resistance 116 and electronic part 117 are provided from the front on the lower surface of the substrate 112b.

The above mentioned second circuit substrate 113 is a multilayer substrate laminated, for example, in four layers. Its rear end surface coincides with the end surface of the above mentioned substrate 112b. The substrate of the fourth layer from below extends forward. By the way, the substrate of the first layer forming the second circuit substrate 113 and the circuit substrate 112b forming the first circuit substrate 112 are electrically connected with each other by the bonding wire 21 on the rear end surfaces.

Electronic parts 117 and a transmitting element 118 are provided from the front on the upper surface of the substrate of the fourth layer forming the above mentioned second circuit substrate 113. Further, an IC chip 19 wire-bonded with the substrate of the fourth layer is provided on the lower surface of the substrate of the fourth layer.

The above mentioned transmitting element 118 is provided with a transmitting antenna 119 in the rear so as to extend out of the rear end surface of the TV camera body 101.

By the way, the objective frame 104, switch 114 and transmitting antenna 119 are air-tightly bonded with the TV camera body 101 which is filled with an inert gas.

Now, the observed image formed on the imaging surface of the solid state imaging chip 12 is photoelectrically converted, is output as an image signal and is processed to produce a so-called composite video signal including a synchronous signal, for example, of an NTSC system. Then, this composite video signal is converted to such high frequency wave as of a UHF band by the transmitting element 118 formed, for example, of an RF modulator and is transmitted as an electric wave from the transmitting antenna 119. This electric wave is received by an antenna, for example, of an ordinary television receiver not illustrated and is demodulated by this television receiver and the observed image of this television receiver is displayed.

According to this embodiment, the TV camera body 101 can be made smallest in the contour, is made wireless and therefore can be improved in the handlability.

Figure 14:
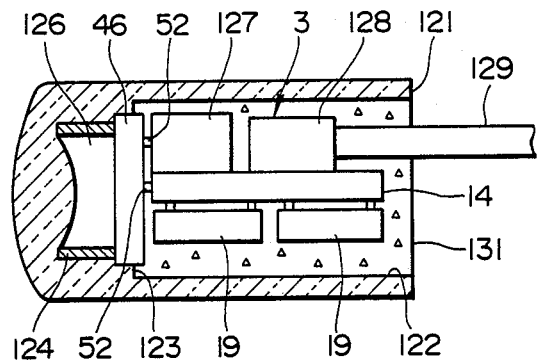
FIG. 14 is an explanatory view of an imaging apparatus of the tenth embodiment of the present invention.

FIG. 14 is an explanatory view of an imaging apparatus of the tenth embodiment of the present invention.

An imaging apparatus 3 is contained within a housing 121 formed to be substantially columnar. This housing 121 is formed of such light transmitting resin as, for example, plastics, has a smooth convex spherical surface by a radius of curvature on the front end surface and is provided with a recess 122 on the rear end surface. On the rear end surface 123 within this recess 122, a solid state imaging chip 46, for example, of a back surface illuminating type is embedded with the imaging surface directed forward, with the center of the imaging surface coinciding with the center line of the rotation of the housing 121 and further with the opposite imaging surface of the solid state imaging chip 46 exposed within the recess.

A cylindrical light intercepting tube 124 is provided with the rear end surface in contact with the imaging surface of the above mentioned solid state imaging chip 46. A hollow part 126 is formed within the light intercepting tube 124. The front end surface of this hollow part 126, that is, the housing 121 is formed to be a rearward convex smooth spherical surface by a radius of curvature and is to form a two-surface nonspherical lens together with the convex spherical surface formed on the front end surface of the above mentioned housing 121.

A circuit substrate 14 is provided in parallel with the center line of the rotation of the housing 121 in the rear of the above mentioned solid state imaging chip 46. The front end surface of this circuit substrate 14 and the opposite imaging surface of the solid state imaging chip 46 are face-bonded with each other by a bump 52. On the front part of the upper surface of the circuit substrate 14, the end surface of an electronic part 127 is provided to coincide with the front end surface of the circuit substrate 14 and is face-bonded to the opposite imaging surface of the solid state imaging chip 46 through a bump 52 the same as of the circuit substrate 14. Further, on the upper surface of the circuit substrate 14, a transmitter-receiver 128 having such electromotive force generating means as a solar battery and such laser generating means as a semiconductor laser is provided as connected with an optical fiber cable 129 as signal lines having transmitting courses of the two systems. Also, IC chips 19 are respectively face-bonded on the lower surface of the circuit substrate 14.

By the way, the above mentioned optical fiber cable 129 is connected at the tip to a controlling apparatus not illustrated having a photoelectric converting circuit and an electric power feeding laser generating means.

The above mentioned circuit substrate 14, IC chips 19, electronic part 127 and transmitter-receiver 128 are made to be contained within the projected area in the optical axial direction of the solid state imaging chip 46. Further, the above mentioned circuit substrate 14, IC chips 19, electronic part 127, transmitter-receiver 128 and optical fiber cable 129 in the front end part are made to be contained within the above mentioned recess 122. The space within this recess 122 is filled with such sealing material 131 settable by ultraviolet rays as, for example, a photosetting resin to seal the contained electronic parts.

Now, the laser light emitted from the electric power feeding laser generating means provided within the controlling apparatus not illustrated is transmitted through one course of the optical fiber cable 129, is input into the transmitter-receiver 128, is received by the solar battery and is converted to an electric power to be able to be fed to the respective electronic parts forming the solid state imaging apparatus 3.

The electronic part 127 forming a driver circuit fed with the electric power as mentioned above delivers a driving clock to the solid state imaging chip 12. The observed image formed on the imaging surface of the solid state imaging chip 12 is photoelectrically converted and is output as a picture image signal. This picture image signal is processed to produce a composite video signal. The luminous intensity of the semiconductor laser provided in the transmitter-receiver 128 is directly modulated by this composite video signal and a video information signal is delivered to the other course of the optical fiber cable 129 and is converted to a composite video signal by a photoelectrically converting circuit not illustrated to display the observed image in a monitor not illustrated. By the way, the modulating system may encode the pulses of the semiconductor laser by the FM modulation, PFM modulation or PWM modulation.

According to this embodiment, by making the housing also a lens, the number of parts can be reduced and the outside diameter of the solid state imaging apparatus 3 can be made smaller. Further, as the electronic parts are sealed with a photosetting resin, the producing process can be simplified.

Figure 15:
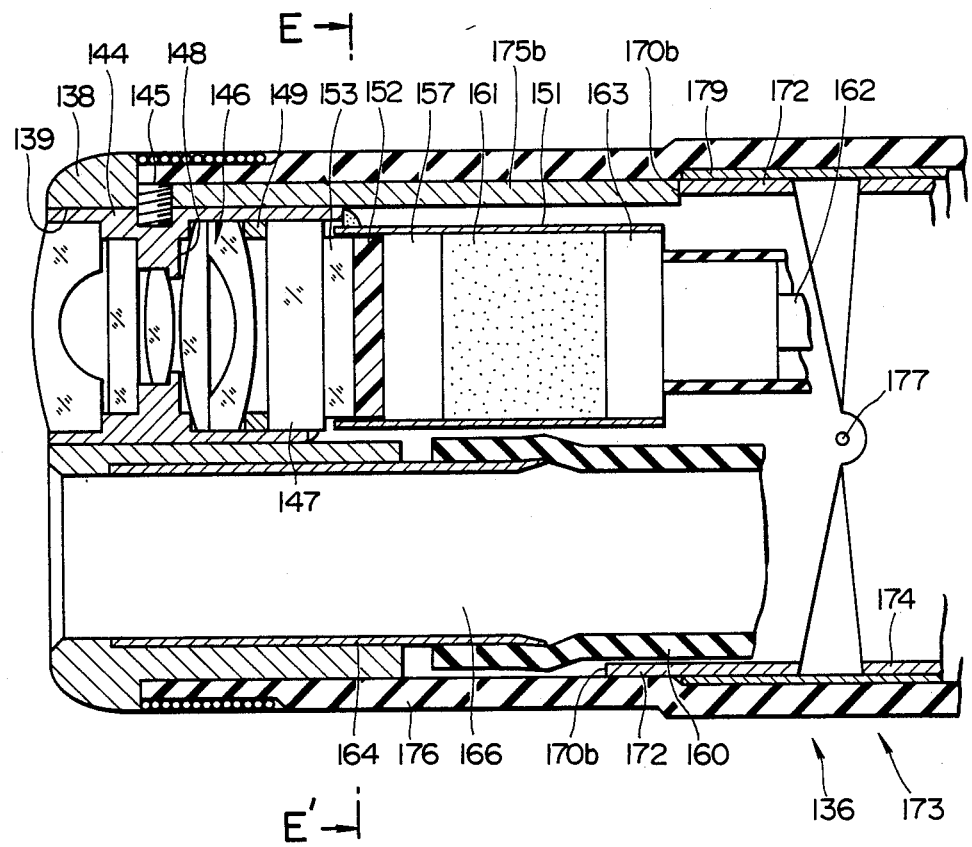
FIGS. 15 to 17 relate to the eleventh embodiment of the present invention.
Figure 16:
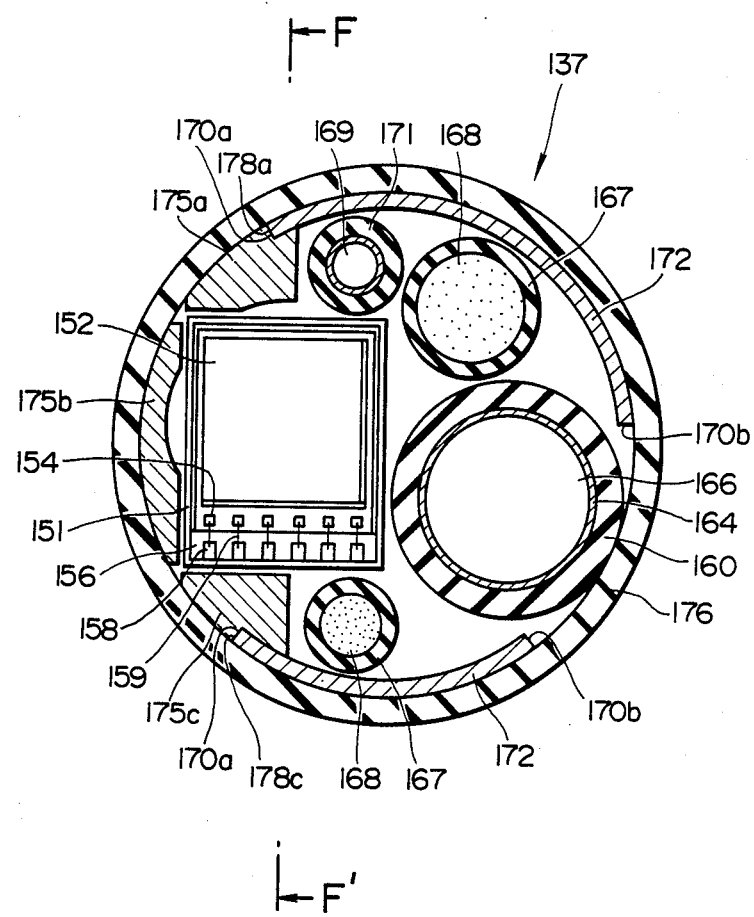
Figure 17:
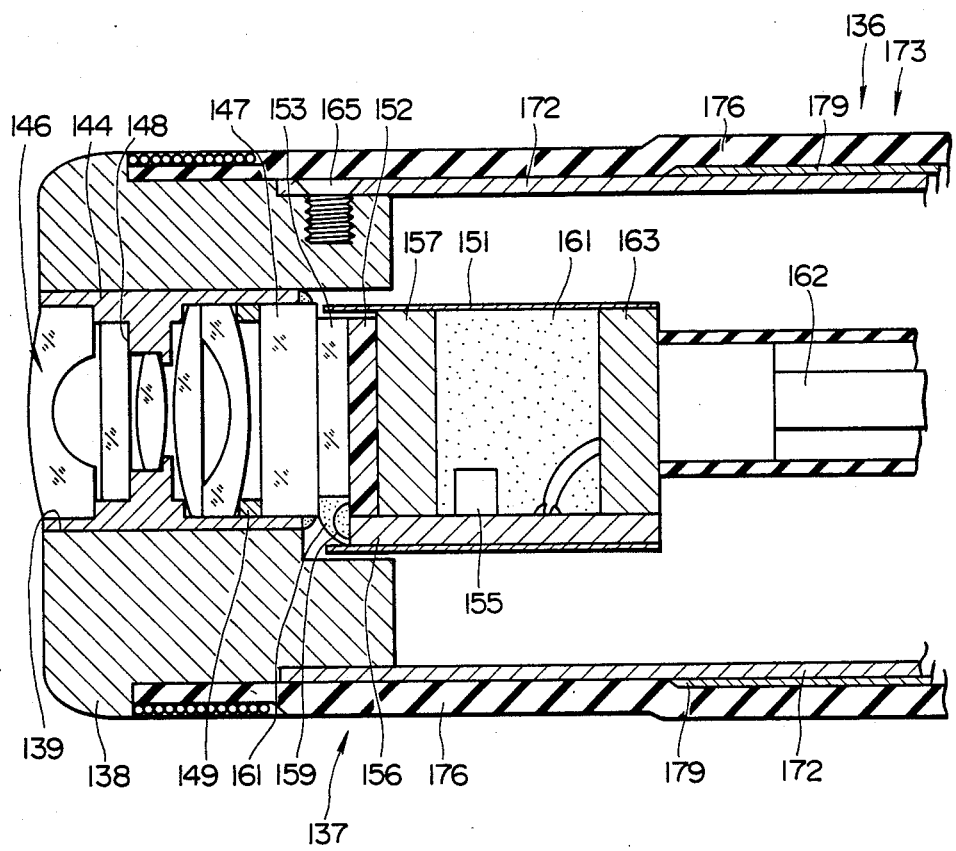

FIGS. 15 to 17 relate to the eleventh embodiment of the present invention. FIG. 15 is a magnified sectioned view of an endoscope tip part. FIG. 16 is a sectioned view in the direction E—E' in FIG. 15. FIG. 17 is a sectioned view in the direction F—F' in FIG. 16.

The tip part 137 of an endoscope insertable part 136 is provided with a substantially columnar tip forming member 138 made of such rigid material as, for example, a metal. An observing through hole 139 passing parallelly in the lengthwise direction through the above mentioned insertable part 136 and forceps channel through hole 141 and an illuminating through hole and air and water feeding channel through hole not illustrated are formed in the above mentioned tip forming member 138.

By the way, the tip forming member 138 may be of a plastic molding, ceramic molding or metal die-casting and is preferably insulative. In using a conductive material, it is preferable to apply an insulating coating on the outer periphery.

An objective frame 144 is fitted in the above mentioned observing through hole 139 and is positioned by a positioning pin 145. In the above mentioned objective frame 144, an objective system 146 and circular second cover glass 147 are positioned by a step 148 of the objection frame 144 and a spacer 149 and are fitted. By the way, the focus is adjusted by varying the thickness of the spacer 149.

In the rear end part of the above mentioned objective frame 144, such chip supporting frame 151 as, for example, a shielding film is inserted and fixed and a solid state imaging chip 152 arranged so as to have the imaging surface positioned in the image forming position of the above mentioned objective system 146 is held by the above mentioned chip supporting frame 151. By the way, the objective frame 144 and chip supporting frame 151 are electrically connected with each other.

On the image area provided with an optical black of the above mentioned solid state imaging chip 152, a square first cover glass 153 which is also a color filter array wherein color filters respectively transmitting three primary colors, for example, of red(R), green(G) and blue(B) are arranged in the form of a mosaic or the like is provided as overlapped and is bonded so that the light path center of the above mentioned optical system 146 may coincide. For example, six bonding pads 154 on the chip side are provided on one somewhat widened side on the periphery of the image area.

Such circuit substrate 156 as, for example, a multilayer ceramic substrate on which such electronic part 155 as, for example, a CCD driving circuit is fitted as in FIG. 17 is arranged within the above mentioned chip supporting frame 151. A die-bonding pad member 157 made, for example, of a metal is mechanically and electrically connected substantially at right angles with the circuit substrate 156 on the front end part of the above mentioned circuit substrate 156.

The above mentioned solid state imaging chip 152 is die-bonded to the front surface of the above mentioned die-bonding pad member 157.

On the front end surface of the above mentioned circuit substrate 156, for example, six base side bonding pads 158 are provided, are connected with chip side bonding pads 154 provided on the solid state imaging chip 152 by bonding wires 159 and are sealed together with the periphery of the solid state imaging chip 152 with such electrically insulating sealing member 161 as, for example, an epoxy resin. At the rear end of the circuit substrate 156, a cable fixing member 163 holding such signal cable 162 as, for example, a shielding wire inserted through the above mentioned insertable part 136 is mechanically and electrically connected substantially at right angles with the circuit substrate 156 and the signal cable 162 passing through the above mentioned cable fixing member 163 is connected to the circuit substrate 156. The space within the chip supporting frame 151 is filled with such sealing member 161 as, for example, an epoxy resin.

On the other hand, a forceps channel connecting pipe 164 is fitted to the rear end side of the above mentioned forceps channel through hole 141 and is expanded in the diameter in the rear end part to which a forceps channel tube 160 forming a forceps channel 166 is connected as inserted through the insertable part 136.

A light distributing lens system not illustrated is fitted in an illuminating through hole not illustrated and a light guide 168 coated with a tube 167 is connected to the rear end of this light distributing lens system as shown in FIG. 16. An air and water feeding nozzle not illustrated is fitted to an air and water feeding channel through hole not illustrated and is connected with an air and water feeding tube 171 forming an air and water feeding channel 169 as shown in FIG. 16.

By the way, in this embodiment, two above mentioned light guides 168 and one air and water feeding channel 169 are provided.

In the rear end part of the above mentioned tip forming member 138, as in FIG. 16, three extended parts 175a, 175b and 175c are provided near the outer periphery of the chip supporting frame 151 to protect it and the upper and lower extended parts 175a and 175c are provided respectively with steps 178a and 178c fitting later described protective members 172. By the way, the extended parts 175a, 175b, and 175c may be connected with the adjacent extended parts 175a, 175b and 175c.

On the other hand, many substantially annular articulating frames 174 are rotatably connected in the lengthwise direction in a curvable part 173 adjacent to the rear of the above mentioned tip part 137. The foremost articulating frame 174 is rotatably connected to a curving shaft 177 provided in the rear end part of the later described protective member 172.

The above mentioned protective member 172 is substantially annular, is provided with a first incision 170a in the position corresponding to the above mentioned extended parts 175a and 175c and with a second incision 170b near the connecting part of the forceps channel tube 160 with the forceps channel connecting pipe 164 inserted in the forceps channel through hole 141, is externally fitted to the rear end part of the above mentioned tip forming member 138 and is fixed with a fixing screw 165.

The above mentioned articulating frame 174 is contained within a blade 179 knit in the form of a net of such fine wires as of a metal. The above mentioned tip part 137 and curvable part 173 are coated with a coating tube 176 as an outer coating. The tip part of this coating tube 176 is externally fitted to the above mentioned tip forming member 138, is wound, for example, with a thread and is then fixed with a bonding agent.

In this embodiment formed as in the above, the objective frame 144 arranged in the tip part forming member 138 and the chip supporting frame 151 containing the solid state imaging chip 152, circuit substrate 156 and cable fixing member 163 are protected by the extended parts 175a, 175b and 175c and the light guide 168 and air and water feeding channel 169 are protected by the protective member 172. For such part in which the contents themselves have a strength as the forceps channel connecting pipe 164, as the protective member 172 is incised, the space within the tip part 137 is effectively used and the diameter can be made smaller by the thickness of the protective member 172.

By the way, if the entire periphery is to be protected by only the tip forming member instead of the conventional protective member, the contents will not be able to be incorporated in the tip forming member. The extended parts may be made only in a part and the other parts may be left open and then covered with the protective member after the contents are incorporated.

In each of the above described embodiments, the solid state imaging apparatus according to the present invention is used for endoscopes and TV cameras. However, the present invention is not restricted to be used only for endoscopes for TV cameras, can be used as an imaging means for electronic still cameras and the like and is effective to make the size smaller.

In this invention, it is apparent that working modes different in a wide range can be formed on the basis of this invention without deviating from the spirit and scope of the invention. This invention is not restricted by its specific working modes except being limited by the appended claims.

What is claimed is:

1. A solid state imaging apparatus comprising:
    an image forming optical system fitted within a lens frame;
    a solid state imaging chip arranged to have its imaging surface positioned in the focal plane of said image forming optical system;
    a circuit substrate to which said solid state imaging chip is directly mechanically affixed substantially at right angles, and to which said solid state imaging chip and a signal cable at the tip are electrically connected; and
    a sealing member in sealing contact with at least a part of the periphery of said solid state imaging chip.

2. A solid state imaging apparatus according to claim 1 wherein said sealing member seals the peripheries of said lens frame, solid state imaging chip and circuit substrate and the tip of said signal cable and is formed to be columnar.

3. A solid state imaging apparatus comprising:
    an image forming optical system fitted within a lens frame:
    a solid state imaging chip arranged to have its imaging surface positioned in the focal plane of said image forming optical system;
    a circuit substrate to which said solid state imaging chip is mechanically fitted substantially at right angles and to which said solid state imaging chip and a signal cable at the tip are electrically connected; and
    a sealing member sealing at least a part of the periphery of said solid state imaging chip;
    said solid state imaging chip being die-bonded to a die-bonding pad member made of a metal.

4. A solid state imaging apparatus comprising:

an image forming optical system fitted within a lens frame;

a solid state imaging chip arranged to have its imaging surface positioned in the focal plane of said image forming optical system;

a circuit substrate to which said solid state imaging chip is directly mechanically affixed substantially at right angle, and to which said solid state imaging chip and a signal cable at the tip are electrically connected;

a sealing member in sealing contact with at least a part of the periphery of said solid state imaging chip; and an electronic part as a peripheral circuit arranged on said circuit substrate.

5. A solid state imaging apparatus according to claim 4 wherein said solid state imaging chip is connected with said circuit substrate by a bonding wire.

6. A solid state imaging apparatus according to claim 4 wherein said sealing member seals the peripheries of said lens frame, image forming optical system, solid state imaging chip, electronic part and circuit substrate and the tip part of said signal cable and is formed to be columnar.

7. A solid state imaging apparatus according to claim 4 wherein said electronic part is at least one of an amplifying circuit, solid state imaging chip driving circuit, matching circuit and cooling element.

8. A solid state imaging apparatus comprising:
an image forming optical system fitted within a lens frame:

a solid state imaging chip arranged to have its imaging surface positioned in the focal plane of said image forming optical system;

a circuit substrate to which said solid state imaging chip is mechanically fitted substantially at right angles and to which said solid state imaging chip and a signal cable at the tip are electrically connected; and a sealing member sealing at least a part of the periphery of said solid state imaging chip;

said solid state imaging chip being die-bonded to a die-bonding pad member made of a metal.

9. A solid state imaging apparatus comprising:
an image forming optical system fitted within a lens frame;

a solid state imaging chip arranged to have its imaging surface positioned in the focal plane of said image forming optical system;

a circuit substrate to which said solid state imaging chip is directly mechanically affixed and to which said solid state imaging chip and a signal cable at the tip are electrically connected; and a sealing member in sealing contact with at least a part of the periphery of said solid state imaging chip.

10. An endoscope insertable part comprising:
an image forming optical system fitted within a lens frame;

a solid state imaging chip arranged to have its imaging surface positioned in the focal plane of said image forming optical system;

a circuit substrate to which said solid state imaging chip is directly mechanically affixed, and to which said solid state imaging chip and a signal cable at the tip are electrically connected; and a sealing member in sealing contact with at least a part of the periphery of said solid state imaging chip.

11. A solid state imaging apparatus comprising:
an image forming optical system fitted within a lens frame:

a solid state imaging chip arranged to have its imaging surface positioned in the focal plane of said image forming optical system;

a circuit substrate to which said solid state imaging chip is mechanically fitted substantially at right angles and to which said solid state imaging chip and a signal cable at the tip are electrically connected; and a sealing member sealing at least a part of the periphery of said solid state imaging chip;

said sealing member being a filling member filling said solid state imaging chip and forming the outside diameter of the endoscope insertable part.

12. A solid state imaging apparatus comprising:
an image forming optical system fitted within a lens frame;

a solid state imaging chip arranged to have its imaging surface positioned in the focal plane of said image forming optical system;

a circuit substrate to which said solid state imaging chip is mechanically fitted and to which said solid state imaging chip and a signal cable at the tip are electrically connected; and a sealing member sealing at least a part of the periphery of said solid state imaging chip;

said sealing member being a filling member filling said solid state imaging chip and forming the outside diameter of the endoscope insertable part;

said solid state imaging chip being die-bonded on at least a part of the surface to a conductive die-bonding pad member.

* * * * *